(12) United States Patent  
Chmelik

(10) Patent No.: US 12,048,559 B2
(45) Date of Patent: Jul. 30, 2024

(54) APPARATUS FOR AIDING RELAXATION

(71) Applicant: BIOSELF TECHNOLOGY LTD, Manningtree (GB)

(72) Inventor: Stefan Chmelik, London (GB)

(73) Assignee: BIOSELF TECHNOLOGY LTD., Manningtree (GB)

( * ) Notice: Subject to any disclaimer, the term of this patent is extended or adjusted under 35 U.S.C. 154(b) by 1101 days.

(21) Appl. No.: 15/755,480

(22) PCT Filed: Aug. 25, 2016

(86) PCT No.: PCT/EP2016/001429
§ 371 (c)(1),
(2) Date: Feb. 26, 2018

(87) PCT Pub. No.: WO2017/071785
PCT Pub. Date: May 4, 2017

(65) Prior Publication Data
US 2020/0245931 A1    Aug. 6, 2020

(30) Foreign Application Priority Data

Aug. 26, 2015 (GB) ..................... 1515177

(51) Int. Cl.
*A61B 5/00* (2006.01)
*A61B 5/0205* (2006.01)
*A61B 5/145* (2006.01)

(52) U.S. Cl.
CPC .......... *A61B 5/4884* (2013.01); *A61B 5/0051* (2013.01); *A61B 5/0205* (2013.01);
(Continued)

(58) Field of Classification Search
CPC ... A61B 5/4884; A61B 5/0051; A61B 5/0205; A61B 5/14539; A61B 5/486;
(Continued)

(56) References Cited

U.S. PATENT DOCUMENTS 5,687,244 A * 11/1997 Untersander .......... H04R 9/066
381/151
2004/0152957 A1    8/2004 Stivoric et al.
(Continued)

FOREIGN PATENT DOCUMENTS

GB      2 458 389 A     9/2009
JP      2008529576      8/2008
(Continued)

OTHER PUBLICATIONS

International Search Report and Written Opinion dated May 2, 2017.
(Continued)

*Primary Examiner* — William J Levicky
(74) *Attorney, Agent, or Firm* — Dority & Manning, P.A.

(57) ABSTRACT

An apparatus for aiding the self-regulation of stress, including a vibrating element vibratable at varying frequencies of vibration, and heart signals or breathing signals monitoring means, and a data processing means. The data processing means includes means for calculating a stress indicator value, based on the heart signals or the breathing signals and that the data processing means includes a means of determining a mechanical vibration rhythm, based on the stress indicator value, including vibrations of one or more frequencies, which is induced in the vibratable element. The data processing means is configured, to create continuous real time feedback loop between the measured heart or breathing rate and calculated stress indicator value and the induced vibration rhythms. Attaching means are included, which can be a strap or harness, or attachments for articles of clothing, for attaching the apparatus to the user—such that the vibrating element of the apparatus is located in the thoracic region of the user's body.

12 Claims, 19 Drawing Sheets

(52) U.S. Cl.
CPC .......... *A61B 5/14539* (2013.01); *A61B 5/486* (2013.01); *A61B 5/6831* (2013.01); *A61B 5/7296* (2013.01); *A61B 2560/04* (2013.01); *A61B 2562/0261* (2013.01); *A61B 2562/0271* (2013.01)

(58) Field of Classification Search
CPC . A61B 5/6831; A61B 5/7296; A61B 2560/04; A61B 2562/0261; A61B 2562/0271
See application file for complete search history.

(56) References Cited

U.S. PATENT DOCUMENTS

| | | | |
|---|---|---|---|
| 2005/0131273 A1 | 6/2005 | Asano et al. | |
| 2008/0214944 A1* | 9/2008 | Morris | A61B 5/486 600/509 |
| 2010/0036280 A1* | 2/2010 | Ballegaard | A61B 5/4824 600/552 |
| 2013/0276785 A1* | 10/2013 | Melker | G16H 20/17 128/204.23 |
| 2014/0077945 A1* | 3/2014 | Amagai | A61B 5/486 340/539.11 |
| 2014/0288435 A1* | 9/2014 | Richards | A61B 5/1123 600/479 |
| 2014/0288472 A1* | 9/2014 | Ehrenreich | A61B 5/02208 601/46 |
| 2014/0371516 A1* | 12/2014 | Tsai | A61B 5/4836 600/14 |
| 2016/0346501 A1* | 12/2016 | Hooper | A61B 5/4836 |

FOREIGN PATENT DOCUMENTS

| | | |
|---|---|---|
| WO | WO 2015/052376 A1 | 4/2015 |
| WO | WO 2015/122846 A1 | 8/2015 |
| WO | WO 2015118302 A2 | 8/2015 |

OTHER PUBLICATIONS

European Examination Report dated Dec. 17, 2018 for EP 16834271.5.

* cited by examiner

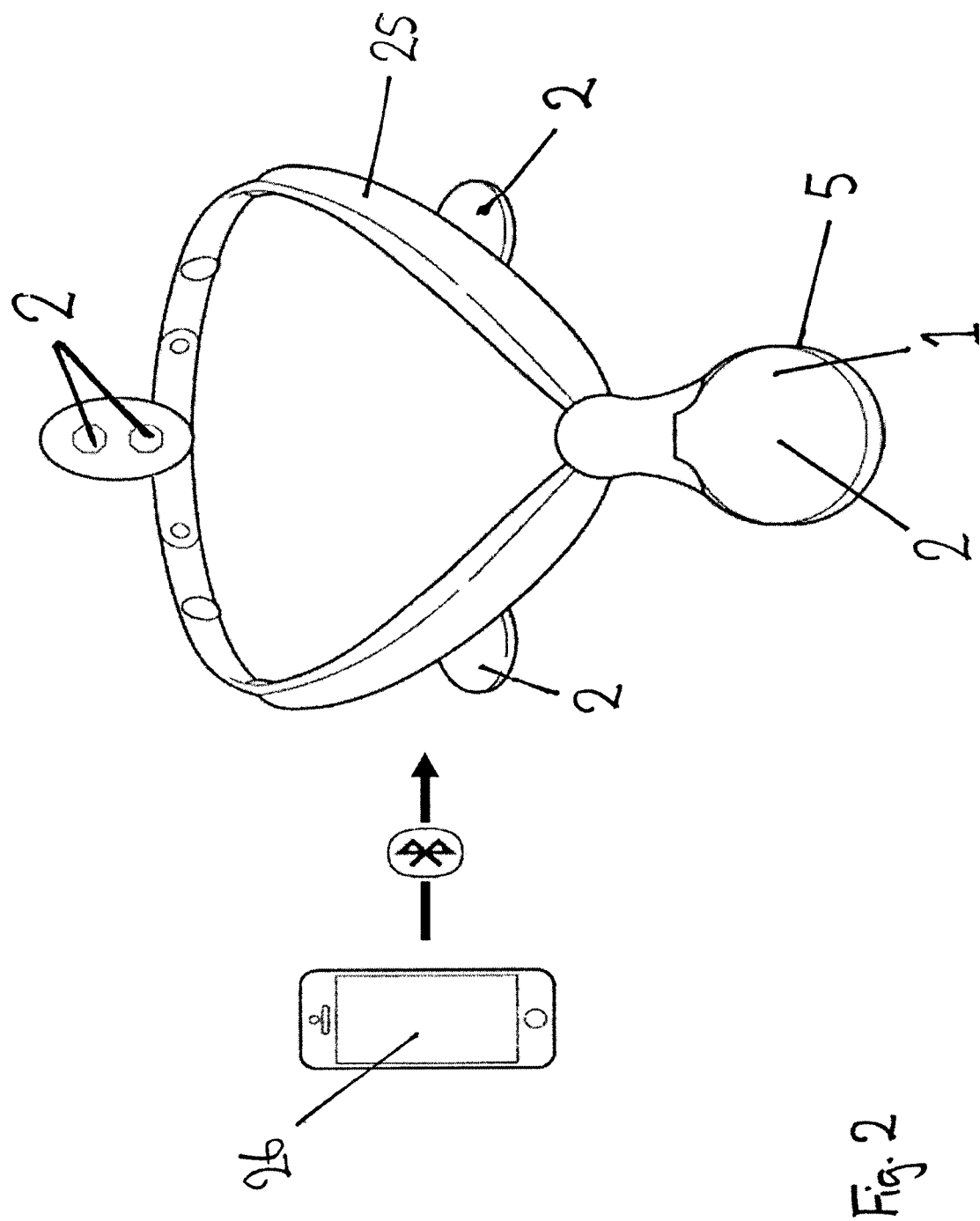

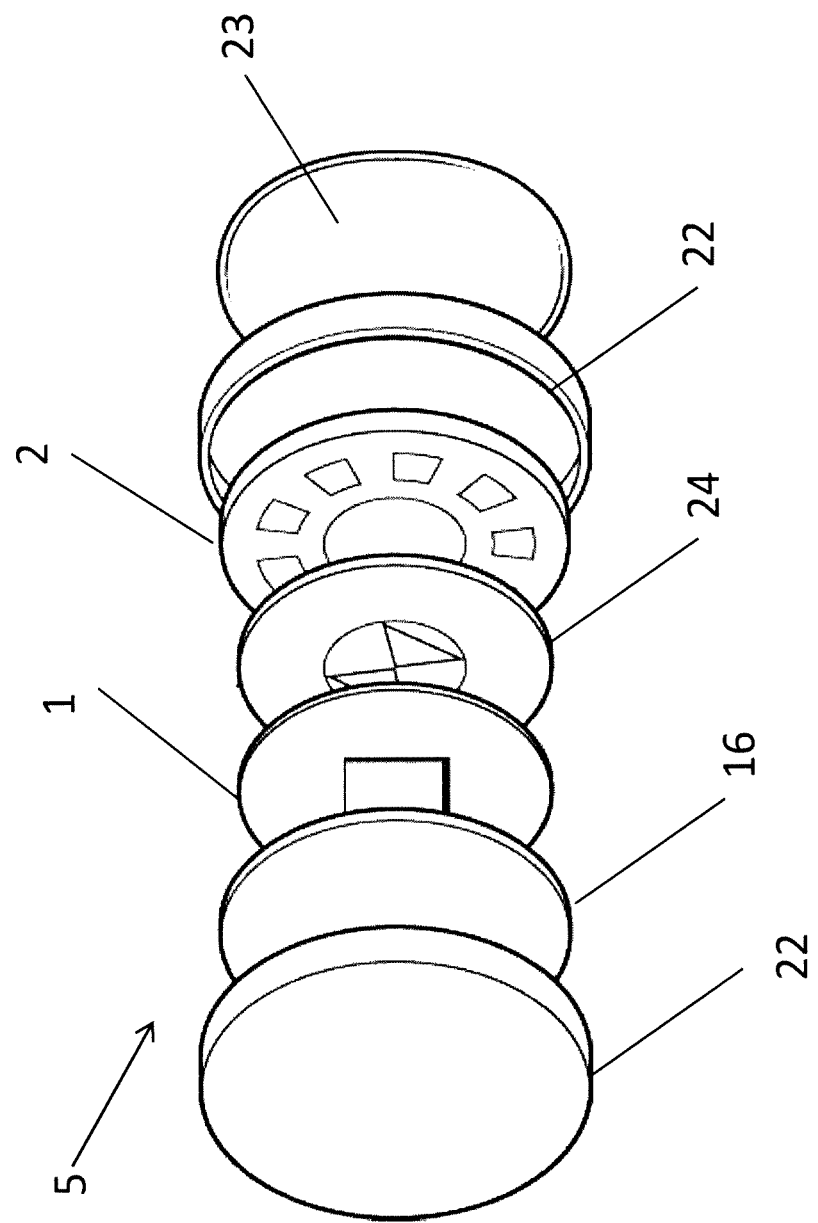

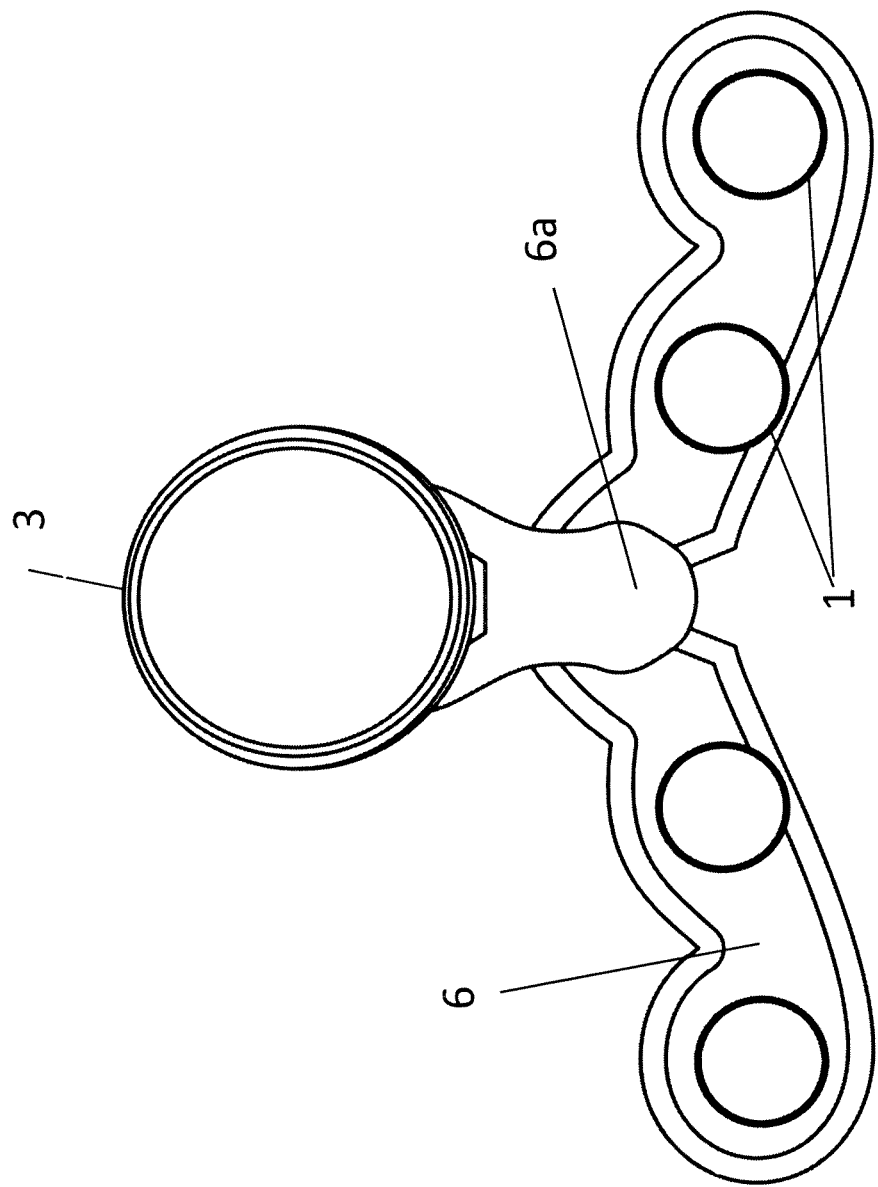

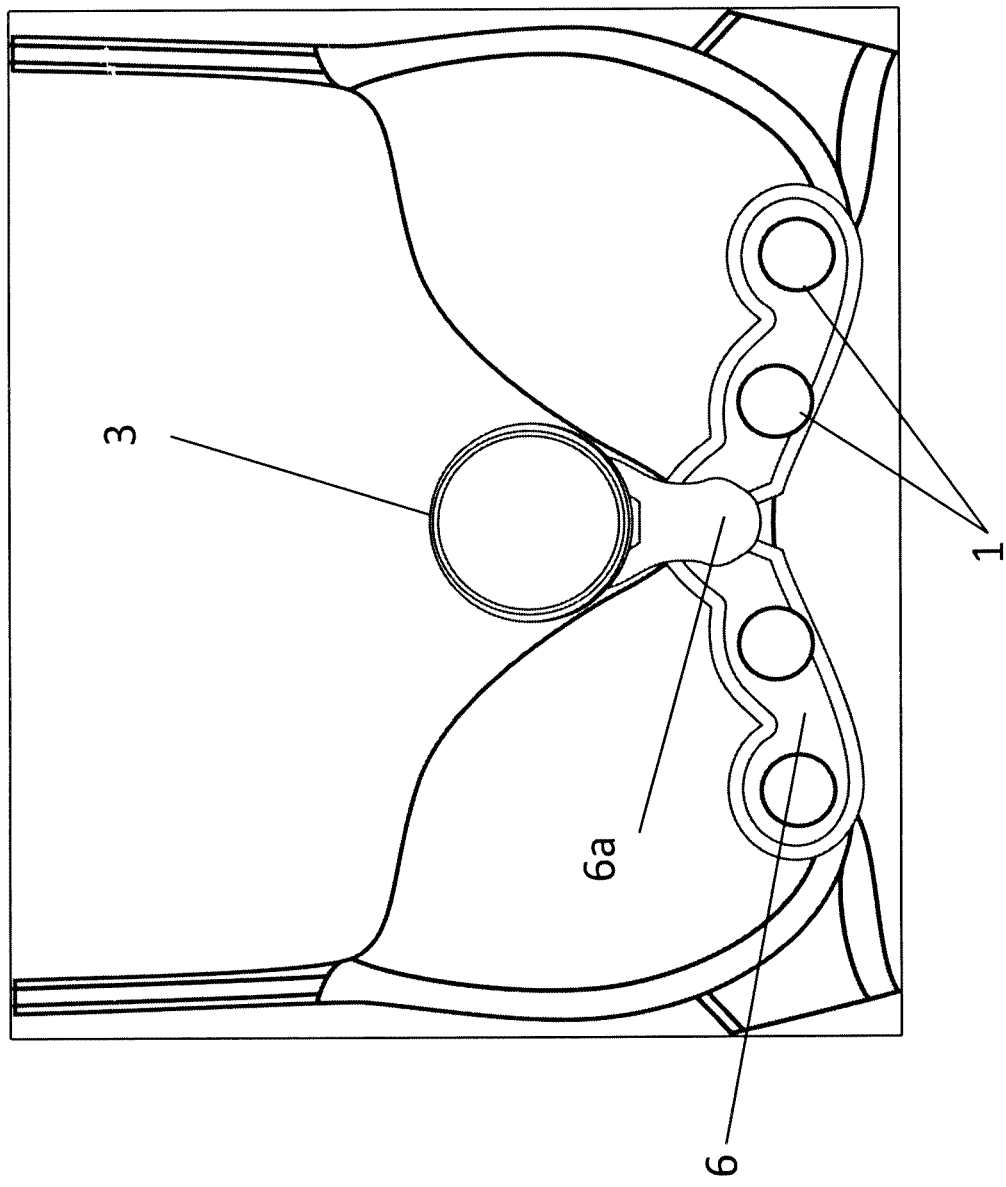

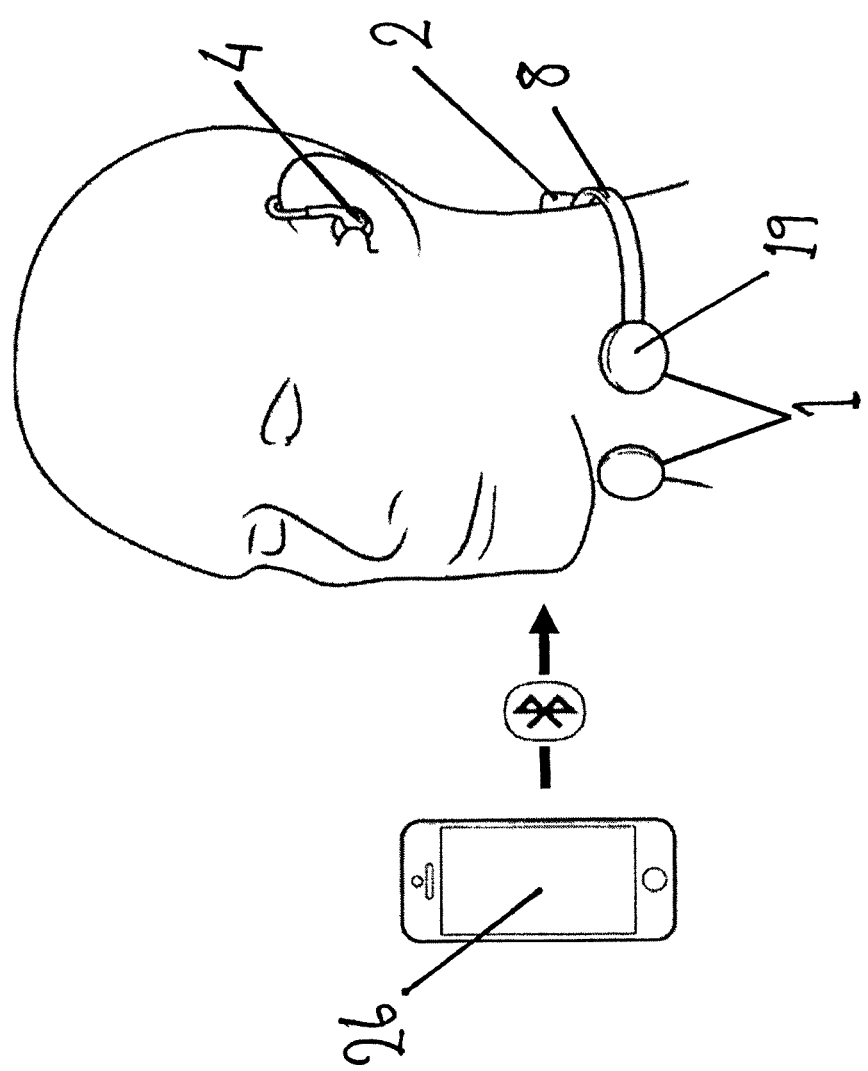

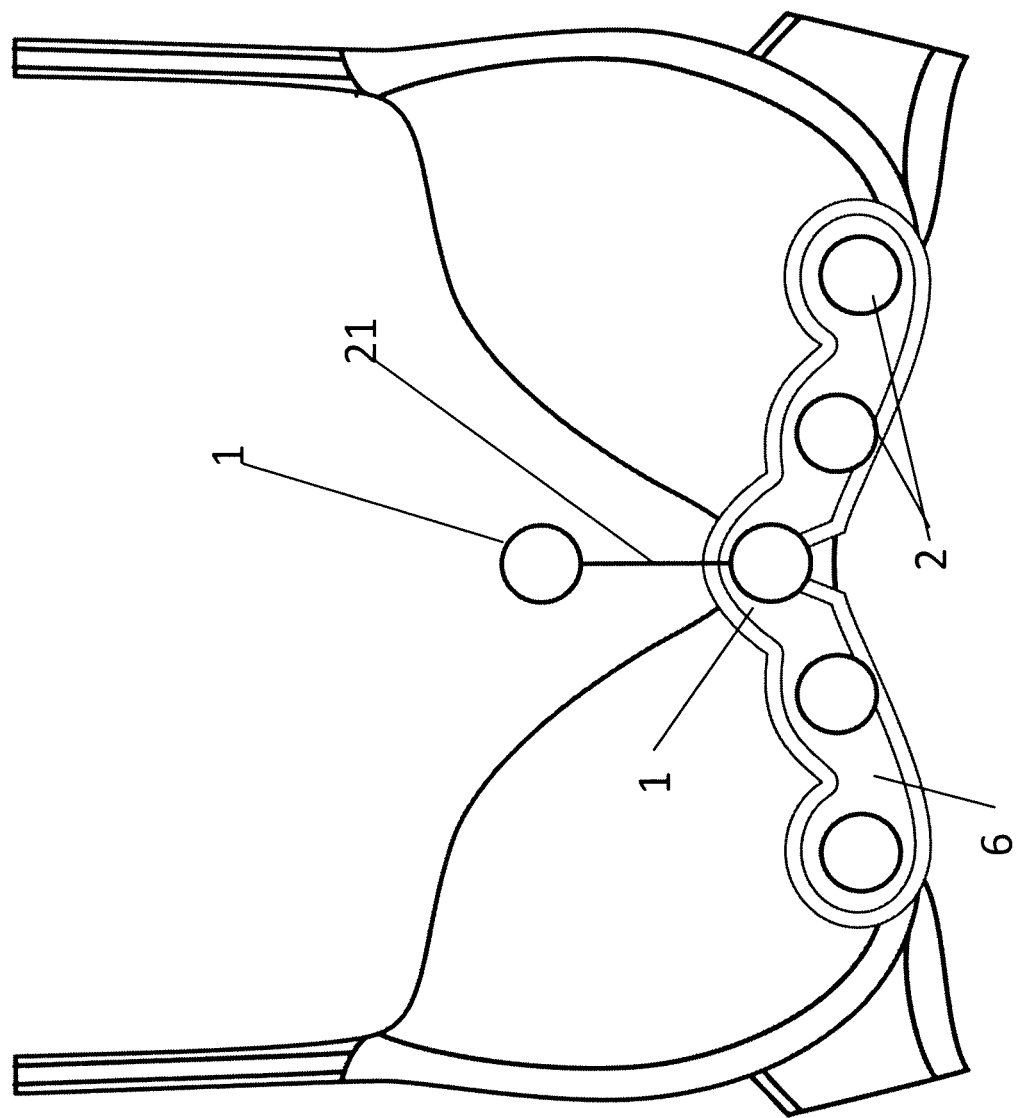

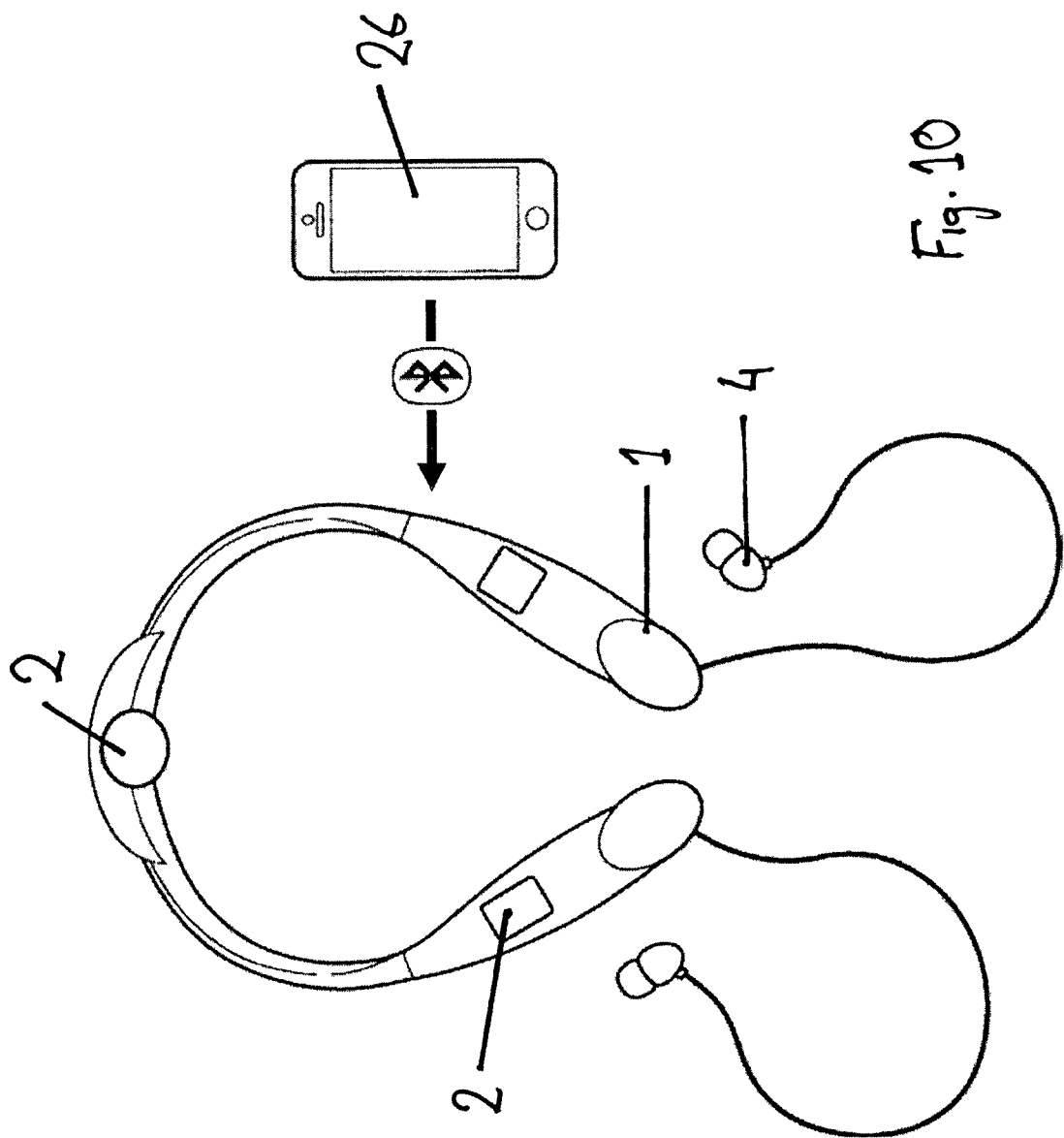

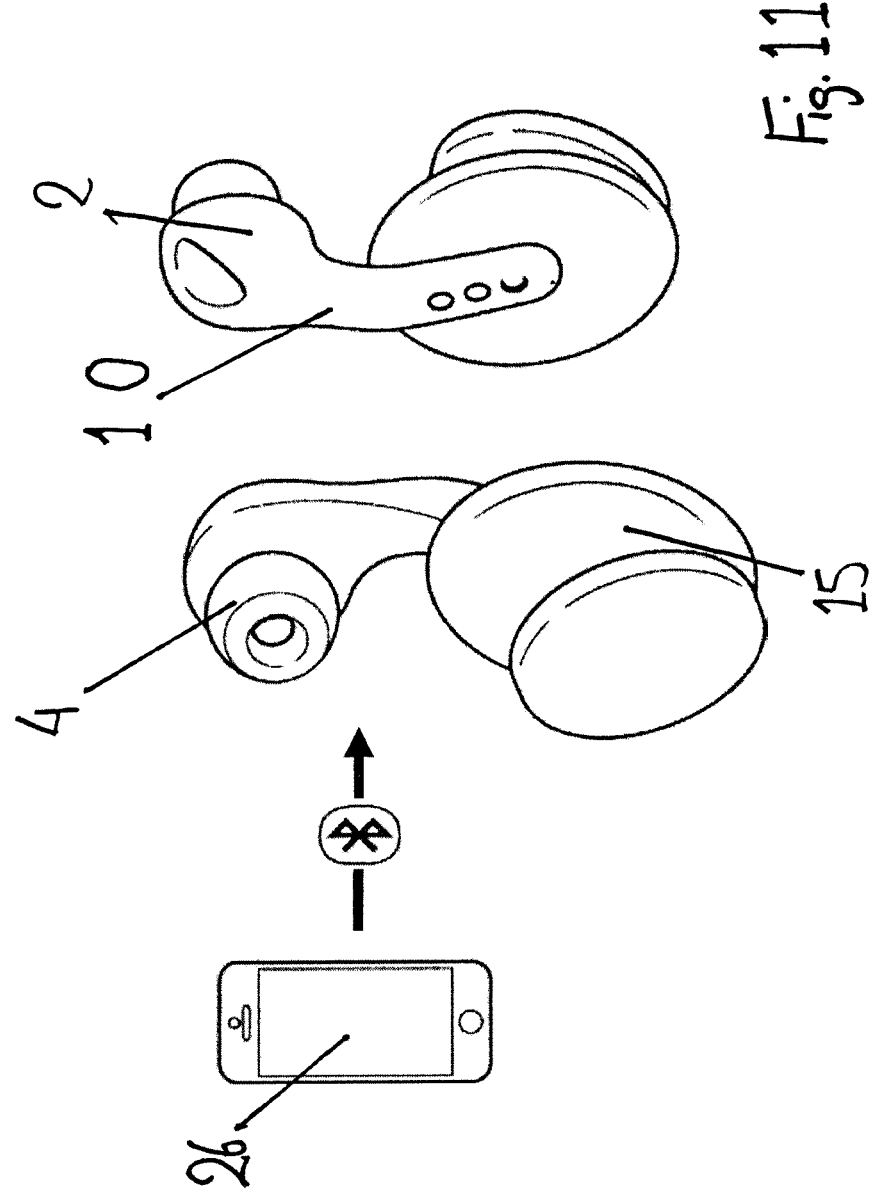

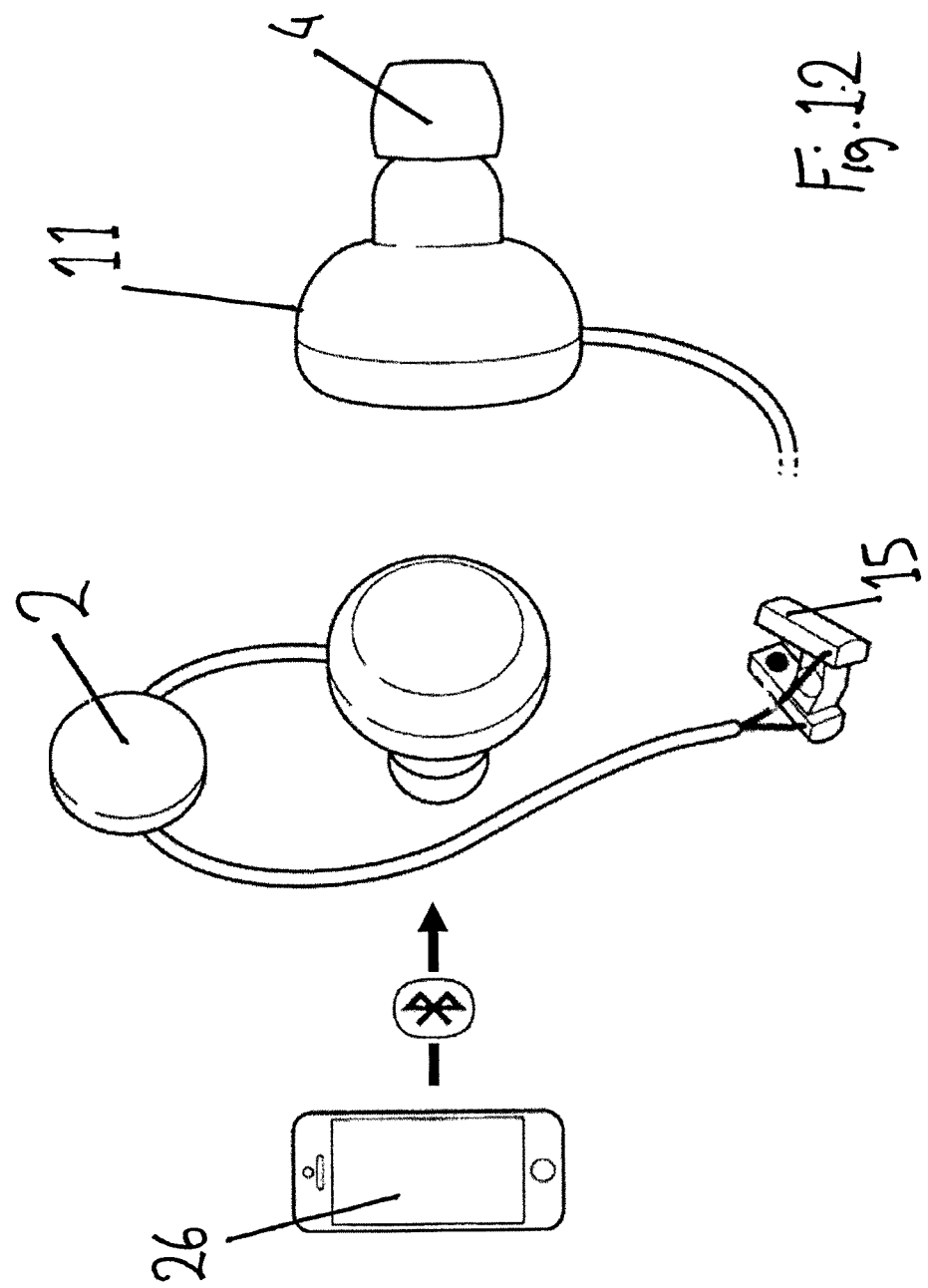

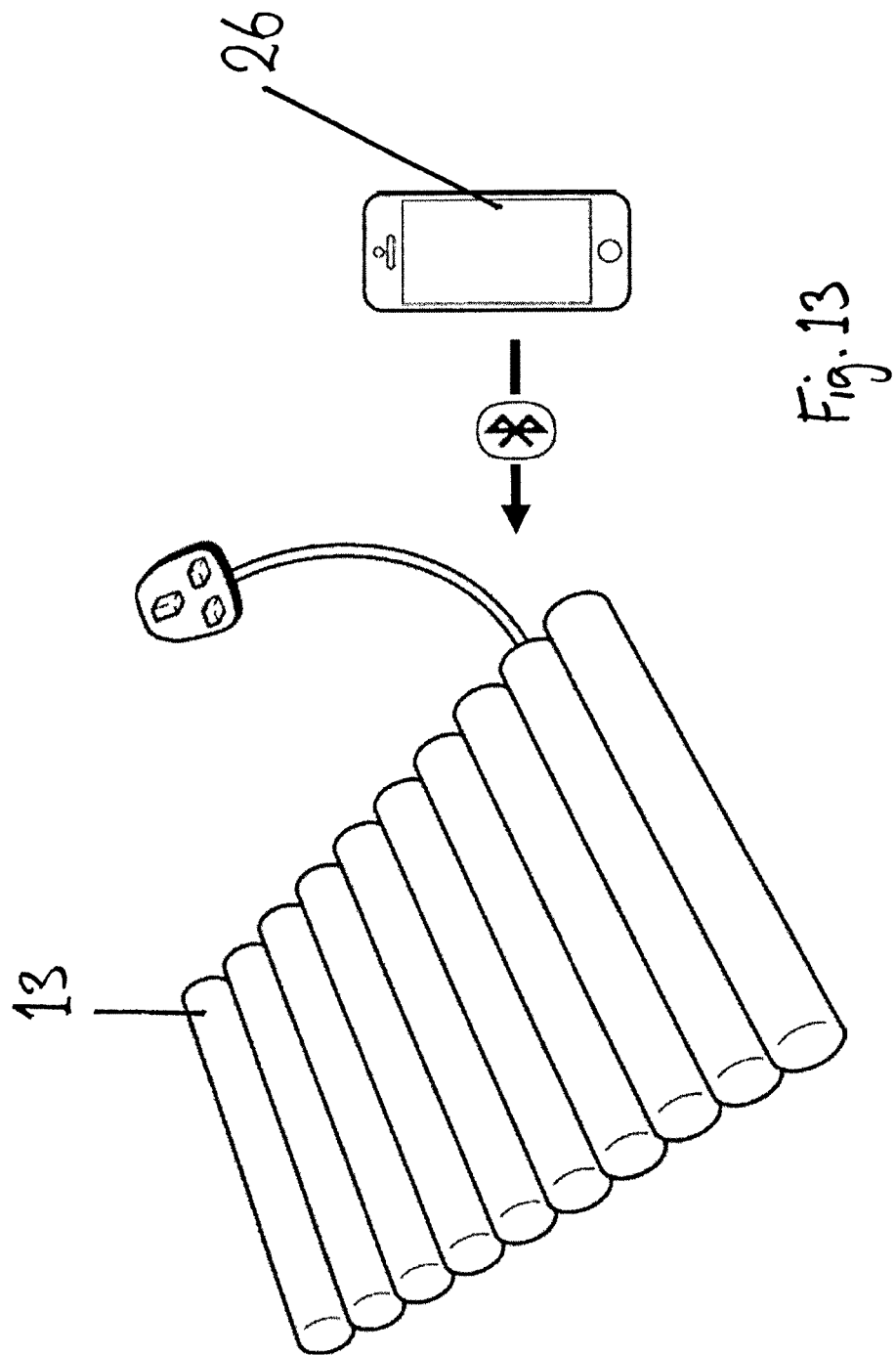

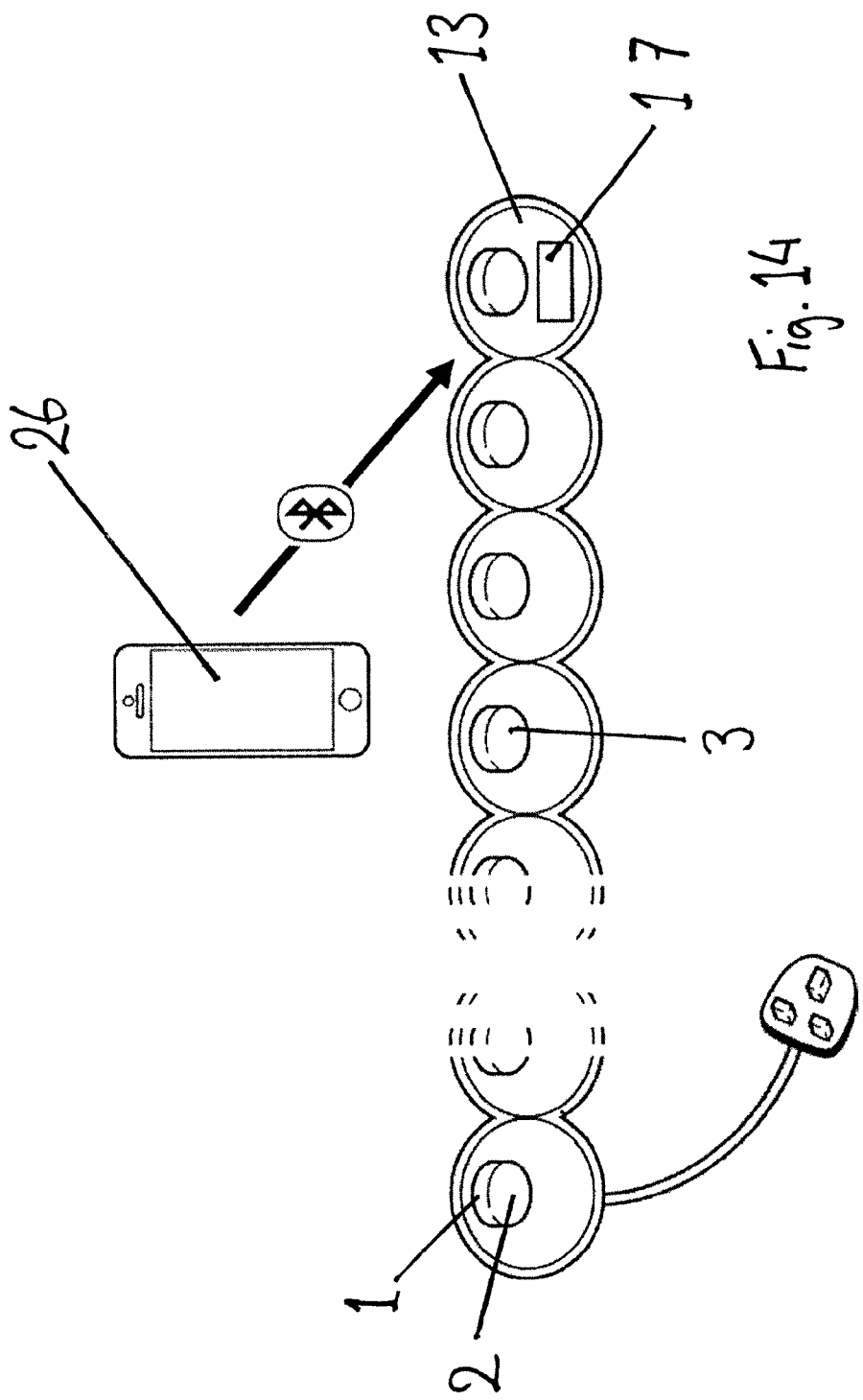

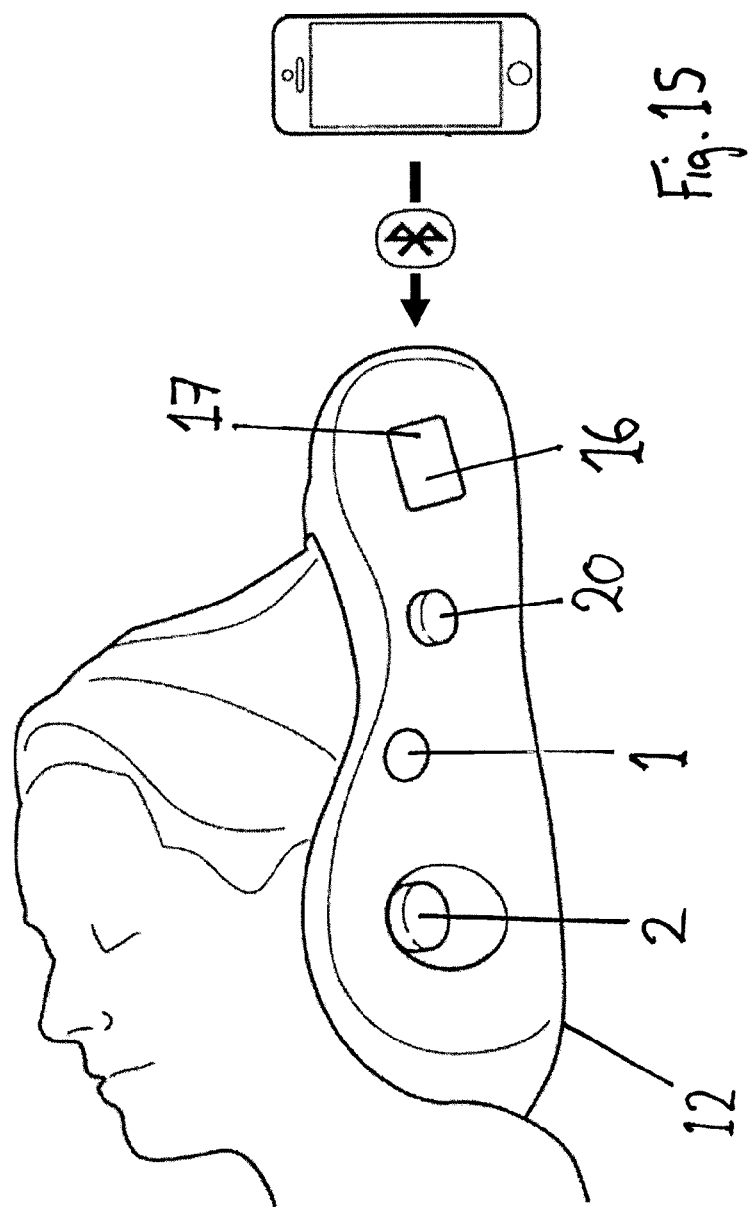

APPARATUS FOR AIDING RELAXATION

This application claims the benefit of Great Britain patent application No. 1515177.2, filed Aug. 26, 2015, which is hereby incorporated by reference in its entirety.

BACKGROUND

Wearable biometric devices are growing in popularity among health conscious technology users. The ability to measure, track and evaluate health indicating variables over a long period of time is a useful tool in gaining insight in to a user's overall health. These biometric devices are often accompanied with software for processing data into fitness information. This information can be displayed as a graph over time or measured against other variables to give health advice such as "eat less" or "run more". Current collectable data includes heart rate, step count, distance travelled, travel speed and oxygen saturation.

However, the current collectable data is a crude measurement of overall health. It is restricted to a very narrow understanding of the health of the user.

The current biometric devices give a very poor indication of overall wellbeing and mental state.

Mindfulness has revolutionized the practice of psychotherapy, meditation and self-awareness and has become a common method for aiding in wellbeing and stress alleviation. These therapies however, are often time consuming and can often take years to learn how to do correctly.

According to Yuval Noah Harari (author of Sapiens: A Brief History of Humankind) and Daniel Kahneman (founder of Behavioral Economics, author of Thinking, Fast and Slow), human beings have evolved to be made happy by one thing and one thing only—pleasant physical sensations in their bodies.

According to Daniel J Seigalj neuroscientist, Mindfulness promotes the nine middle prefrontal brain functions:
1 Bodily regulation
2. Attunement
3. Emotional balance
4 Fear modulation
5. Flexibility of response
6. Insight
7. Empathy
8. Morality
9. Intuition On neural plasticity: "Repeated firing increases synaptic linkages and may lay down myelin, as we become an expert in the skill of knowing the inner world. We can create this repeated firing, coupled with a close focus of attention and sense of emotional engagement, as we voluntarily engage in Mindfulness practice on a regular basis".

SUMMARY

The health markers that are most useful in predicting mental health, stress resilience are: heart rate variability, subjective wellbeing, vagal tone, autonomic resilience and low frequency brain waves such as alpha, theta and delta waves.

Accordingly embodiments of the present invention aim to assist users in their relaxation and meditation techniques.

According to embodiments of the invention there is provided an apparatus for aiding the self-regulation of stress, comprising at least one vibratable element and a means of inducing vibration in the vibratable element at varying frequencies of vibration, a heart signals or breathing signals monitoring means, and a data processing means, characterised in that the data processing means includes means for calculating a stress indicator value, based on the heart signals or the breathing signals and that the data processing means includes. a means of determining a mechanical vibration rhythm, based on the stress indicator value, including vibrations of one or more frequencies, which is induced in the vibratable element.

BRIEF DESCRIPTION OF THE DRAWINGS

Several embodiments of the invention will now be described in references to the appended figures, in which.
FIG. 2 shows a further implementation of the embodiment of FIG. 1,
FIG. 3 shows an enlarged and exploded perspective view of the components of the first embodiment of the invention,
FIG. 8 shows a front view of a further embodiment to the embodiment of FIG. 6,
FIG. 9 shows a front view of the embodiment of FIG. 8 attached to a garment,
FIG. 9a shows a further implementation of the embodiment of FIG. 6,
FIG. 10 shows an above view of the sixth embodiment of the present invention,
FIG. 11 shows a side view of a seventh embodiment of the present invention,
FIG. 12 shows a side view of an eighth embodiment of the present invention,
FIG. 13 shows an above view of a ninth embodiment of the present invention,
FIG. 14 shows a cross-section view of the ninth embodiment of the present invention,
and
FIG. 15 shows a cross-section view of a tenth embodiment of the present invention.

DETAILED DESCRIPTION

Figure 1:
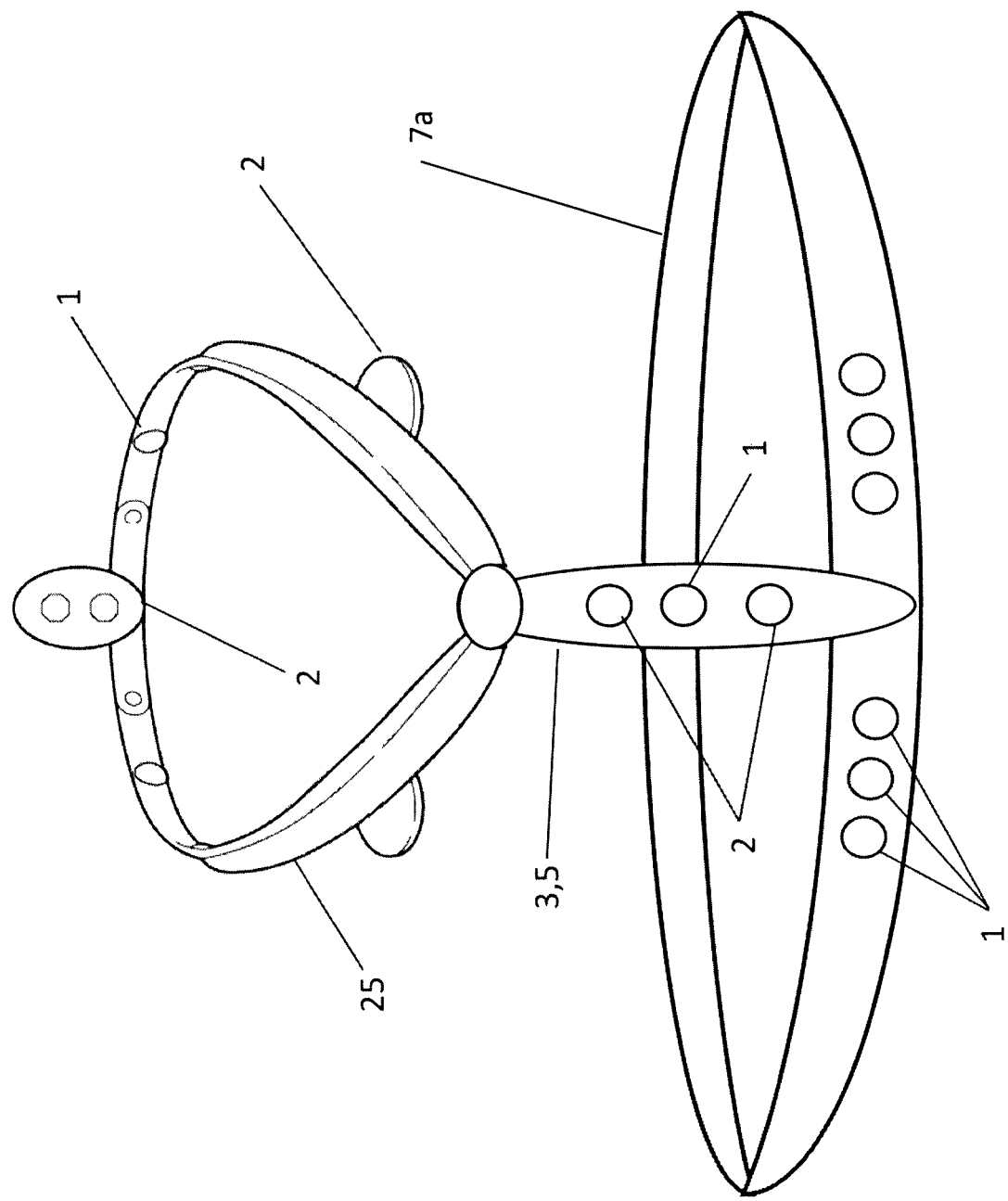
FIG. 1 shows a first embodiment of the invention.

The figures disclose various apparatus for-regulating biological rhythms and assisting meditation, each comprising at least one vibratable element and a means of inducing vibration in the vibratable element at varying frequencies of vibration. Also included in this main embodiment is at least one heart rate monitoring means and a breathing rate monitoring means, and a data processing means. The data processing means includes means for calculating the heart rate variability based on the heart rate measurement and the breathing rate measurement and a means of determining a vibration rhythm, based on the calculated heart rate variability, including vibrations of at least two frequencies, which is induced in the vibratable element.

By this means it is possible to provide passive non-visual biofeedback, distinguishing it from and in contrast to classical meditation and neuro/biofeedback based approaches that involve following a visual or simple audio cue. The use of passive neuromodulation allows the brainstem (where the vagus nerve originates) to receive signals directly and bypasses the frontal lobe, thus eliminating obstruction of the re-training process by the logical brain i.e. limbic vs frontal lobe psychology. Referring specifically to the Figures, the apparatus includes a heart signal monitor, a breathing signal monitor, a data processing unit 26, and an actuator 27, which comprises a vibratable element 2 and a de vice for creating vibrations. Many of the below embodiments will include at least one biopotential electrode 1, which is used for sensing the heat and breathing signals. Some embodiments include other sensors.

The data processing unit calculates a stress indication value based on a time sequence of heart signals and breathing signals as shown in FIG. 3. In this embodiment the stress indication value is derived solely from the heart signals. This is done by deriving the heart Variability rate (HRV), which itself is calculated from a series of derived RR intervals (Respiratory Rale). This HRV is an indication of the vagal tone which is an important factor in determining the stress indication value. These calculated values are used to generate a correspond vibration rhythm and are continuously being, generated as the measurements are continuously made to form a feedback loop, such that a change in the heart rate variability of the user will generate a change in the sequence and/or frequency of vibrations.

The vibrations generated are infrasonic, being less than about 50 hertz. These vibrations can be generated directly by a Vibrating element vibrating at the required frequency, or by means of a binaural beat. Best results have been determined with infrasonic vibrations of less than 30 hertz.

Biological rhythms are defined in the art as neuronal rhythms such as measured by electroencephalogram (EEG), heart rate and variability as measured by electrocardiogram (ECG), basal electrical rhythm of the gastrointestinal tract, respiration rate, vagal tone as expressed by heart rate variability and further measureable bodily rhythms. The apparatus detects signals of these rhythms and generates a vibrational rhythm accordingly, based on some predetermined criteria and also based on data gathered during the sensing and feedback process.

The data processing means is programmed to select from a variety of rhythms from a data storage means and to manage the feedback process such that if a particular rhythm is not having a positive effect on the stress indication value, then an alternative rhythm will be selected, until a selected rhythm does have a positive effect in reducing the stress indicator value. The data storage means also include means of storing the identity of a particular user and the rhythms that have been effective in reducing the stress indication value for that particular user so that these rhythms can be prioritised on subsequent uses of the apparatus.

Figure 1A:
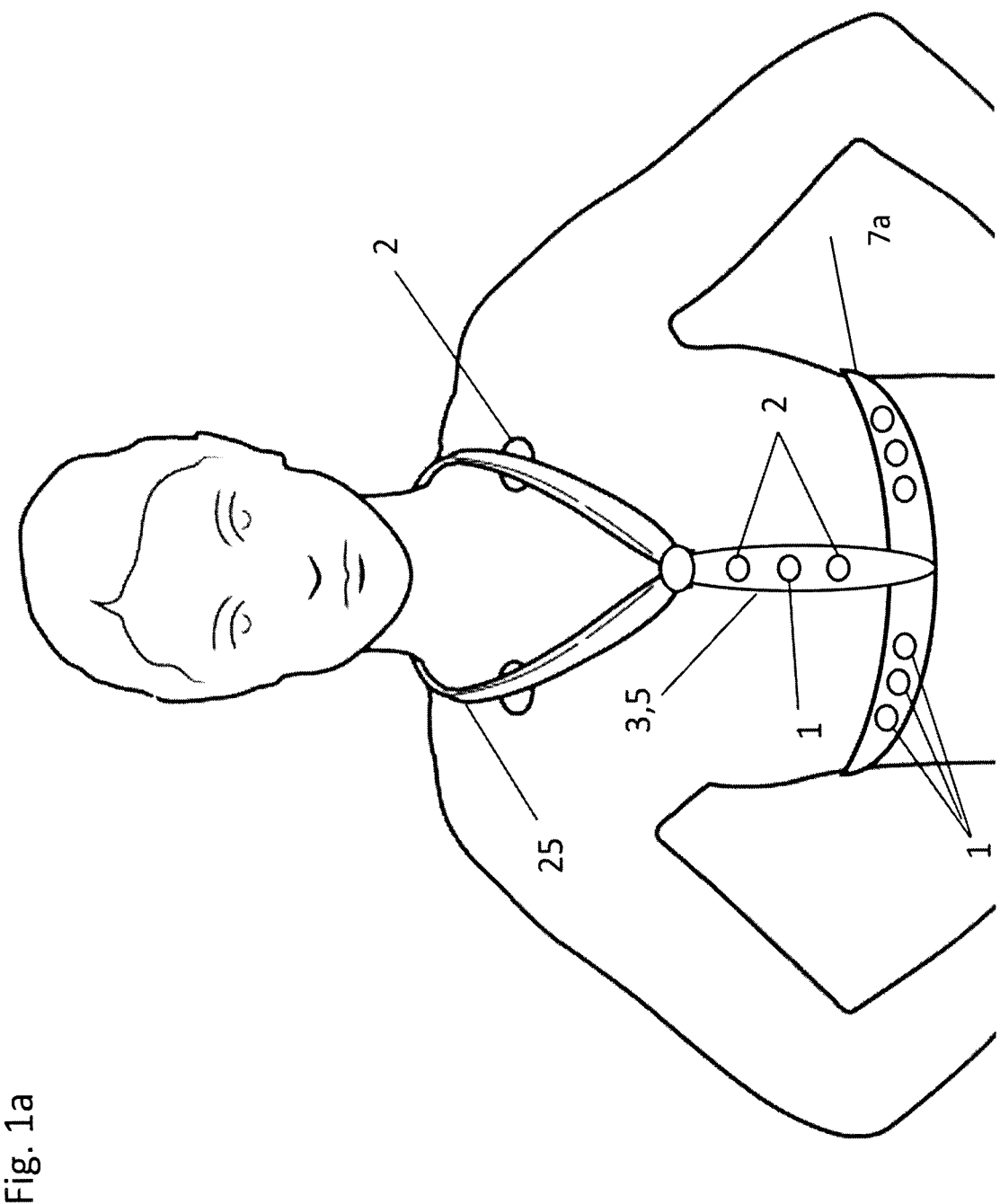
FIG. 1a shows the embodiment of FIG. 1 worn on a user.

In the implementation of this first embodiment of the present invention, as shown in FIGS. 1 and 1*a*, the biopotential sensors 1 are positioned around the circumference of a neck pendant 5 and around the circumference of the body harness including a chest band 7*a* with the main apparatus body 3 including the vibrating means 2 positioned approximately in the centre of the neck pendant. The neck pendant 5 includes body contacting surface which is preferably in contact with the user's sternum so that the vibration can be transferred via bone conduction. There are further vibrators 2 positioned around the lanyard 25 approximately in contact with the clavicle bone, occipital bone and cranial vertebrae. The biopotential sensors 1 measure the skin surface electrical potential, these can be used to measure the heart rate and the breathing rate from which the heart rate variability is calculated providing an indication of the cardiac vagal tone. The sensors 1 and vibrators 2 are in good electrical and vibrational contact preferably through the use of disposable hydrogel pads 23 or just through careful design of the harness. These variables are then transmitted either wirelessly or by wire along the lanyard or neck band 8, 25 to the data processing unit 26 located with the main body 3.

The data processing unit 26 then determines the sequence of vibration rhythm. As well as infrasonic vibrations, audible sound frequencies, electrical or other stimulation may also be used to alter or maintain the currently measured biometrics. This is an ongoing process and the sequence of frequencies are changeable dependent of the measured state of the user.

This implementation of the first embodiment is intended to be worn around the neck. The body contacting surface which is preferably in contact with the sternum of the user transmits the vibrations through the sternum and utilises the body's excellent acoustic resonance properties of bone, fascia and aqueous body fluids and tissues to transmit and amplify the vibrations throughout the body.

The apparatus is powered by a battery pack 16 located in the body of the neck pendent 5. The vibrators 2 and the sensors 1 in the lanyard 25 are electrically connected to the apparatus main body 3 by wires located within the lanyard 25.

The data processing unit 26 in the following embodiments is an integral part of the apparatus although it may also be part of a smart phone or other portable electronic computational device nearby, preferably by Bluetooth, where the data is processed via a predetermined algorithm or protocol, or connected to the apparatus via a short range wifi or by wire, depending on the activity of the user as shown in FIG. 2. The data processing unit 26 is "thus connected to the actuator and sensor and comprises and an algorithm which determines the frequency rhythm output to the actuator based on the measured heart rate, breathing rate and calculated heart rate variability.

Figure 2A:
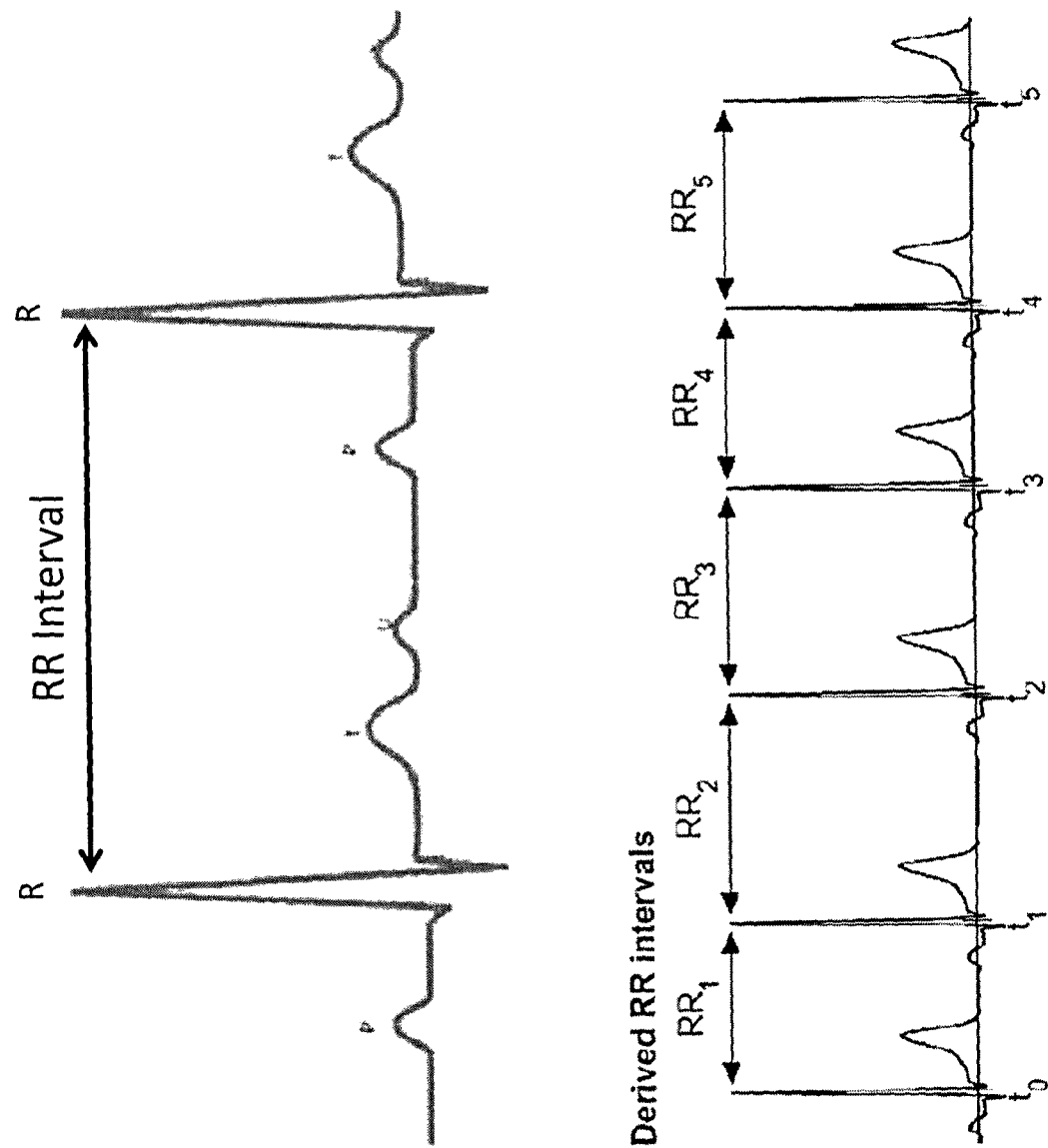
FIG. 2a shows a graph of measured heart rate.

Referring now to FIG. 2*a*, the graph shows the calculation of heart rate variability based upon the measured parameters of the heart rate and the breathing rate. In this embodiment the heart rate variability is calculated by measuring the peak to peak time between each heat between. Alternatively the heart rate variability can be calculated by measuring amplitude of each beat and calculating the difference in amplitude between one beat and the next.

The heart signals and breathing signals can also be sensed by means of one or more microphones.

FIG. 3 shows an enlarged view of the components of the pendent 5, which includes the vibrator 2, including the vibration actuation means 27, biopotential sensor 1 and battery 16 are all contained in a single disc shaped unit. This implementation of the first embodiment also includes a wireless transceiver device 24, a resonance casing 22 and a contact pad 23. The biopotential sensor 1, includes data processing means 26 which converts the sensed parameters, such as the heart and/or breath signals into the heart rate variability value.

Figure 4:
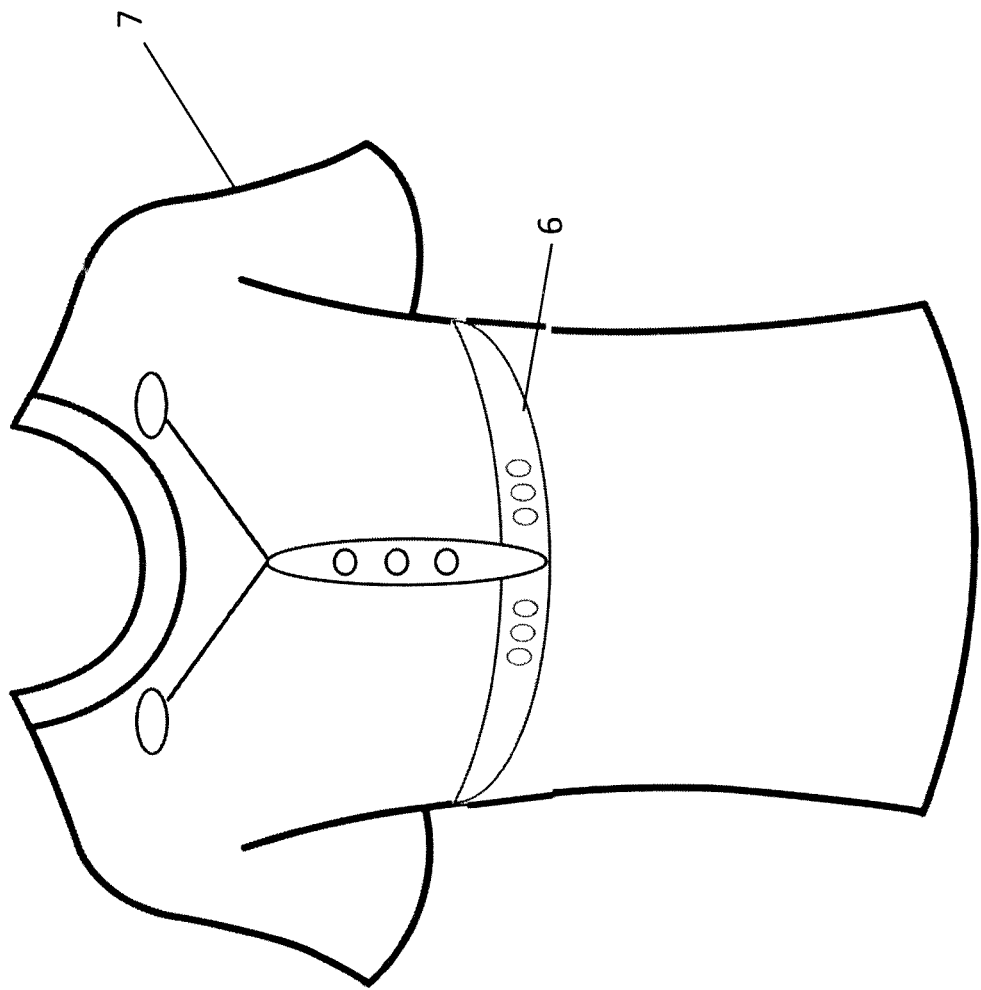
FIG. 4 shows a front view of a second embodiment of the present invention.
Figure 5:
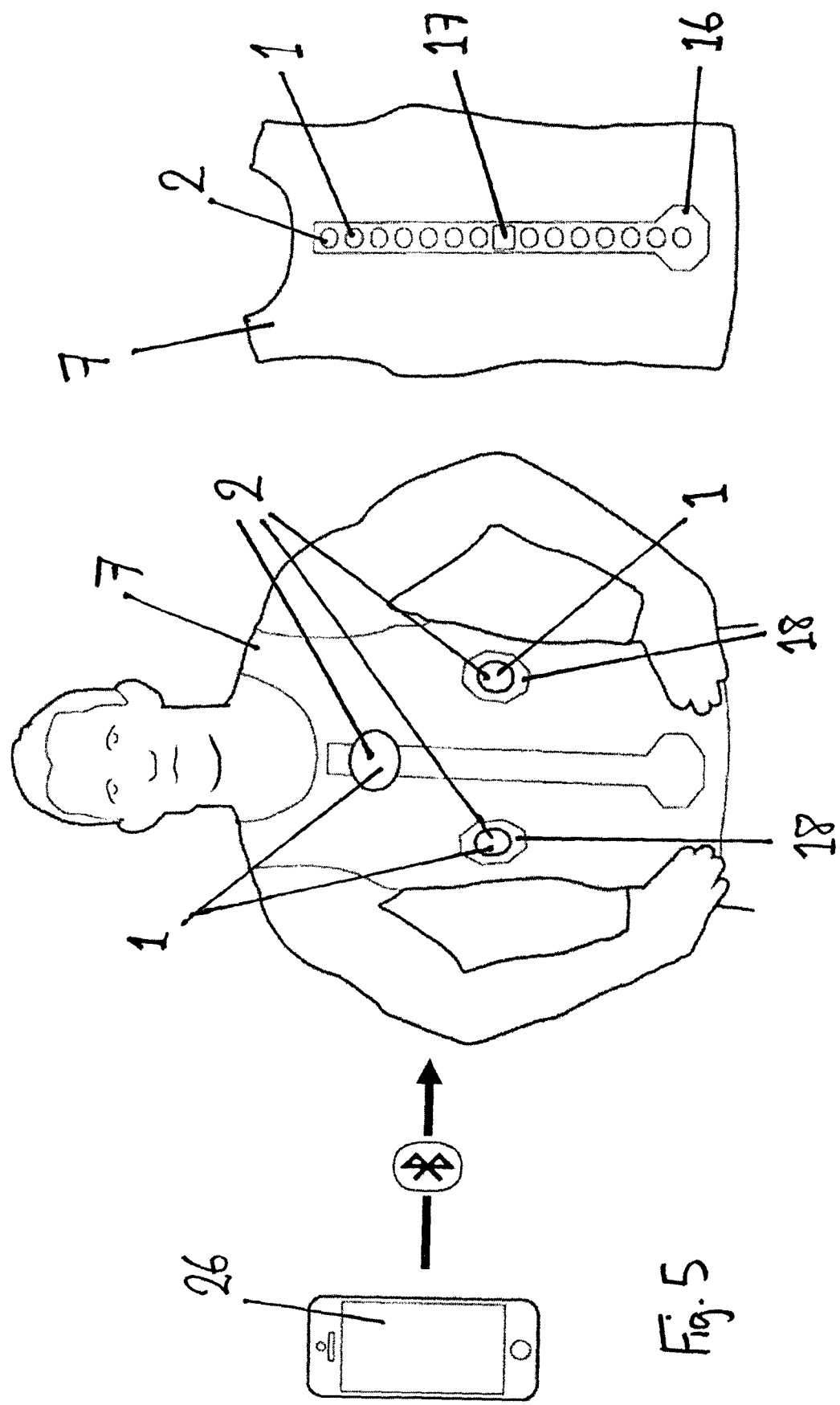
FIG. 5 shows a front view of a third embodiment of the present invention.

FIGS. 4 and 5 show a third embodiment in which the vibrators 2 and biopotential sensors lar e held in place by a smart vest 7. The main apparatus body 3, including the vibration means, data processing means and battery are arranged on an elongate carrier 6 which is attached to the vest 7. The attachment may be by sewing in or incorporating the carrier 6 into the thread of the vest 7. In the implementation of FIG. 5 there are biopotential sensors 1 located approximately in contact with the, sternum, rib cage and spinal column. There are also vibrators 2 located approximately in contact with the sternum, ribcage and spinal column. This embodiment includes stretch receptors 81 located on the later al sides of the smart vest 7 to measure ventilation or respiration rate and along the spinal column and back muscles of the smart vest 7 to measure posture and movement. The smart vest 7 also includes a batter y pack 16 and Bluetooth communicator 17. All components of the smart vest 7 are held in place by the knitted fibres of an article of clothing.

Figure 6:
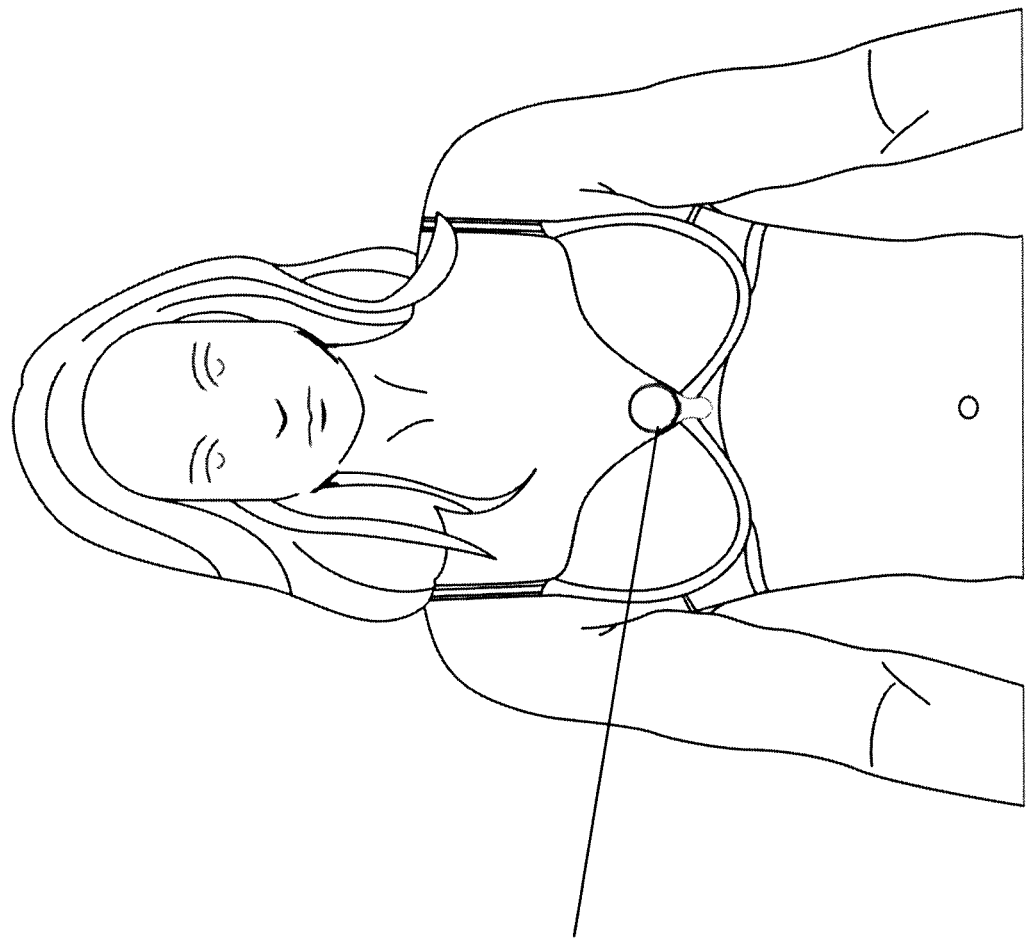
FIG. 6 shows a front view of a fourth embodiment of the present invention.
Figure 7:
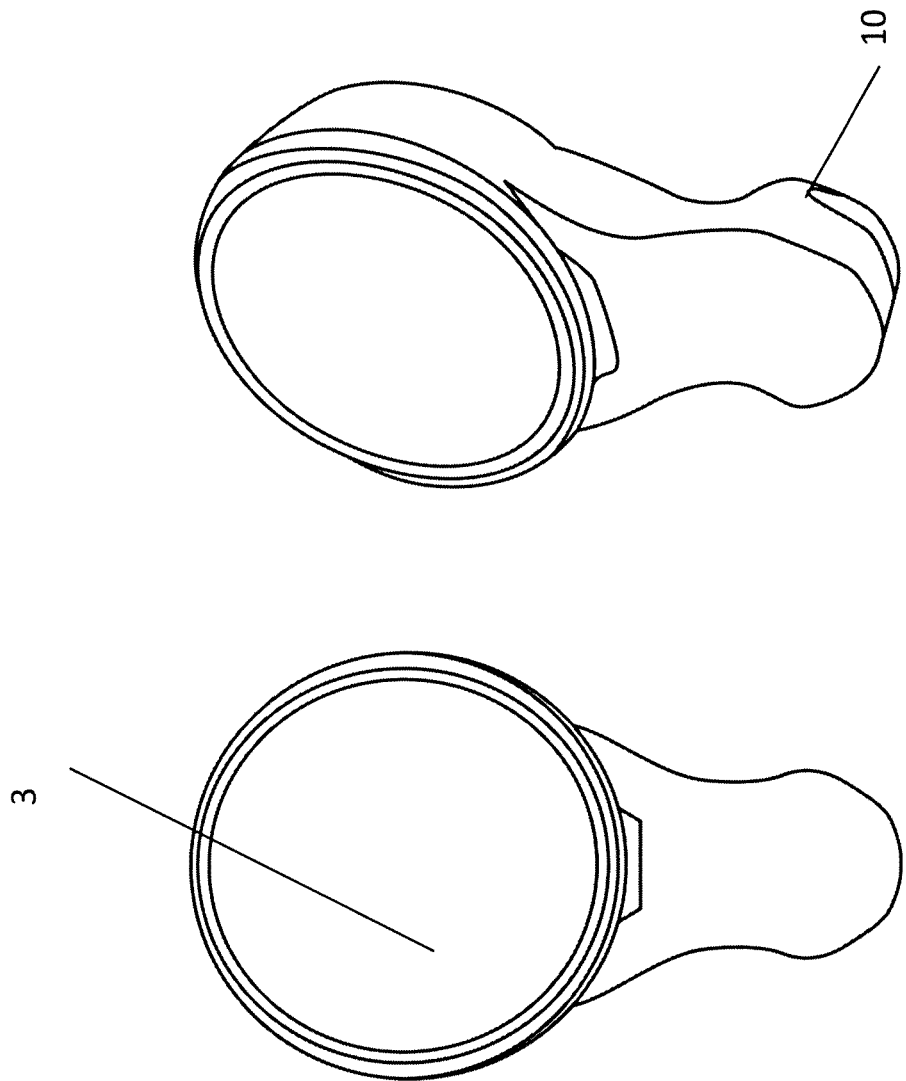
FIG. 7 shows enlarged views of the apparatus of FIG. 6.

FIG. 6 shows a further aspect of the embodiment of FIGS. 4 and 5, with the apparatus body 3 arranged for attachment to an existing garment 7, in this case being a brassier. This allows the apparatus to be ideally located against the sternum of the user. FIG. 7 shows an enlarged view of the apparatus body 3 of the embodiment of FIG. 5 in both front and perspective views showing clip attachment means a6 which is used for releasably attached, and removing the apparatus body from the garment. This would typically be required so the body can be attached for periods of use and removed after use or to wash the garment.

In the embodiment of FIG. 8 a further embodiment is shown in which the main apparatus body 3 is supported on a carrier member 6 which is in turn attached to the garment. The carrier member can be used as a support for other components of the apparatus such as sensors 1, or actuators 2.

FIG. 9 shows the embodiment of FIG. 8 attached to a garment, the garment being a brassier.

FIG. 9a shows a further embodiment with an additional sensor 1 attached to the main apparatus body 3 by a short wire 21.

FIG. 10 shows the sixth embodiment which includes a neck band 8. This neck band 8 is preferably located around the user's neck with the biopotential sensors 1 and electrical stimulators in contact with the carotid sinus of the user, with the purpose of stimulating the vagus nerve. This embodiment also includes vibrating elements 2 located along the length of the band 8.

This neck band 8 is located around the user's neck such that the biopotential sensors 1 and the vibrating elements 2 in contact with the clavicular bone of the user, with the purpose of producing bone conduction stimulation into the thoracic region. This embodiment also includes vibrating elements 2 located at the base of the skull and headphones for audio feedback.

FIG. 11 shows a further embodiment of the invention in which a headphone 4 a vibrator 2 and an ear lobe clip electrode 15 are all included in a biometric earclip 10 This biometric ear clip is preferably attached to the user's ear via the earlobe clip electrode 15 and the headphone 4.

FIG. 12 shows a further embodiment of the present invention which includes a smart headphone 11 comprising a vibrator or vibration actuator 2, a sound inducer also referred to as a headphone 4 and an earlobe clip electrode 15. This embodiment is preferably placed in the user's ear with the earlobe clip electrode 15 attached to the earlobe.

FIGS. 13 and 14 show a further embodiment of the present invention. This embodiment is a mat 31 which includes a number of vibrating elements 2, at least one biopotential sensor land at least one speaker 3. These are arranged in a pre-determined pattern and number of each either on the surface of the mat or preferably embedded within the structure of the mat material to produce a smooth surface for resting on. The user preferably lies down on this mat to use the invention. The mat can be rolled up for portability.

FIG. 15 shows the final embodiment of the present invention which includes a sleep pillow 12 comprising a vibrating element 2, a biopotential sensor 1 and bone conduction speakers 20. Those are preferably in contact with the user's head and neck during use.

COMPONENT LIST

1—Biopotential Sensor
2—Vibrator
3—Apparatus main body
4—Headphones
5—Neck Pendant
6—Carrier
6a—Clip attachment
7—Smart Vest
7a—Chest band
8—Neck Band
9—not used
10—Biometric Ear Clip
11 Smart Headphones
12—Sleep Pillow
13—Sound Mat
14—Headset
15—Ear Lobe Clip Electrode
16—Battery pack
17—Bluetooth communicator
18—Stretch receptors
19—Electrical Stimulators
20—Bone Conduction Speakers
21—Short wire
22.—Resonance Casing
23—Hydrogel Pad
24—Wireless Charging device
25—Lanyard
26—Data Processing Unit
27—Actuator

The invention claimed is:

1. A wearable apparatus for aiding the self-regulation of stress, comprising:
   at least one vibratable element and a vibration actuator for inducing vibration in the vibratable element at, varying frequencies of vibration for transferring vibrations via bone conduction;
   a heart signals monitor; and
   a data processing unit,
   wherein the data processing unit includes a stress indicator value calculator, for calculating a stress indicator value based on the heart signals by deriving the heart rate variability to provide an indication of the vagal tone which determines the stress indicator value; and
   the data processing unit includes a mechanical vibration rhythm determiner, for-determining a mechanical vibration rhythm, based on the stress indicator value, that are continuously being generated to form a real time feedback loop where a change in the heart rate variability will generate a change in the frequency of vibration including vibrations of one or more frequencies induced in the vibratable element for altering the heart rate variability providing an indication of vagal tone;
   wherein the apparatus is configured to be worn such that the vibratable element is positioned on at least one of: the sternum, the ribcage, the clavicle bone, the occipital bone, or the cranial vertebrae; and
   wherein the induced vibrations are at frequencies of less than 50 hertz.

2. An apparatus according to claim 1, wherein the apparatus includes a fastener for attaching the apparatus to the user such that the vibrating element of the apparatus is located in the thoracic region of the user's body.

3. An apparatus according to claim 2, wherein the fastener is a belt or harness that attaches around the user's torso.

4. An apparatus according to claim 2, wherein the apparatus forms part of a garment.

5. An apparatus according to claim 1, further comprising at least one sensor.

6. An apparatus according to claim 5, wherein the at least one sensor includes an electric potential heart sensor.

7. An apparatus according to claim 5, wherein the at least one sensor includes a strain sensor.

8. An apparatus according to claim 5, wherein the at least one sensor includes a temperature sensor.

9. An apparatus according to claim 5, wherein the at least one sensor includes a pH meter.

10. An apparatus according to claim 5, wherein the at least one sensor includes an image sensor.

11. An apparatus according to claim 1, wherein the heart signals monitor includes a motion sensor.

12. An apparatus according to claim 1, wherein the real-time feedback loop regulates neuronal rhythms to below 13 Hertz.

* * * * *